United States Patent
Musa et al.

(10) Patent No.: US 6,528,096 B1
(45) Date of Patent: Mar. 4, 2003

(54) CARRIER MIXED WITH ADDITIVES HAVING LUBRICANT PROPERTIES FOR PREPARING POWDERY PHARMACEUTICAL COMPOSITIONS FOR INHALATION

(75) Inventors: Rossella Musa, Parma (IT); Paolo Ventura, Parma (IT); Paolo Chiesi, Parma (IT)

(73) Assignee: Chiesi Farmaceutical S.p.A., Parma (IT)

( * ) Notice: Subject to any disclaimer, the term of this patent is extended or adjusted under 35 U.S.C. 154(b) by 0 days.

(21) Appl. No.: 09/603,620

(22) Filed: Jun. 26, 2000

Related U.S. Application Data

(63) Continuation-in-part of application No. PCT/EP99/01449, filed on Mar. 5, 1999.

(51) Int. Cl.$^7$ .............. A61K 9/16; A61K 9/14; A61K 9/00
(52) U.S. Cl. .......... 424/490; 424/489; 424/46; 424/400
(58) Field of Search ............ 424/489, 45, 400, 424/490; 514/951

(56) References Cited

U.S. PATENT DOCUMENTS

| | | | |
|---|---|---|---|
| 3,145,146 A | | 8/1964 | Liebermann et al. |
| 5,260,306 A | * | 11/1993 | Boardman et al. |
| 5,376,386 A | * | 12/1994 | Ganderton et al. |
| 5,874,064 A | * | 2/1999 | Edwards et al. |

FOREIGN PATENT DOCUMENTS

| | | |
|---|---|---|
| WO | 87 05213 | 11/1987 |
| WO | 96 23485 | 8/1996 |
| WO | 97/35562 | * 10/1997 |

OTHER PUBLICATIONS

Lindberg: "Evaluation of some tablet lubricants," *Acta Pharm., Suecica* 1972, pp. 207–214.

Peart et al: *Pharmaceutical Reserch*, Nov. 1997, vol. 14, No. 11, p. S–142.

Malamataris, S. et al: "Effect of temperature on the tensile strength of lactose coated with fatty acids. Part 2. Tablets" Powder Technol. (1981), 28(1), 35–42, XP000852784 the whole document.

Podczeck, F., "Particle–particle Adhesion in Pharmaceutial Powder Handling"; Imperial College Press, 1998; pp. 110–115.

Lieberman, H. and Lachman, L., "Pharmaceutical Dosage Forms", Dekker; 1998, pp. 77–85.

* cited by examiner

*Primary Examiner*—Jose' G. Dees
*Assistant Examiner*—Sharmila S Gollamudi
(74) *Attorney, Agent, or Firm*—Nixon & Vanderhye

(57) ABSTRACT

Powdery pharmaceutical compositions including an active ingredient and carrier particles containing only a small amount of lubricant, 0.1–0.5% by weight, are used to prepare dry powder inhalers in order to increase the fine particle dose. A process for coating the surface of the carrier particles with such little amount of lubricant is also provided. Use of limited amount of lubricant is safe and provides ordered stable mixtures without segregation of the active particles during handling and before use.

19 Claims, No Drawings

CARRIER MIXED WITH ADDITIVES HAVING LUBRICANT PROPERTIES FOR PREPARING POWDERY PHARMACEUTICAL COMPOSITIONS FOR INHALATION

This is a continuation-in-part of Application No. PCT/EP99/01449 filed Mar. 5, 1999.

This invention relates to improved powdery pharmaceutical compositions for use in dry powder inhalers. The improvement is concerned with mechanical stability, performances and safety.

Inhalation anti-asthmatics are widely used in the treatment of reversible airway obstruction, inflammation and hyperresponsiveness.

Presently, the most widely used systems for inhalation therapy are the pressurised metered dose inhalers (MDIs) which use a propellant to expel droplets containing the pharmaceutical product to the respiratory. tract.

However, despite their practicality and popularity, MDIs have some disadvantages:

i) the majority of the dose released deposits in the oropharynx by impaction and only a small percentage penetrates directly into the lower lungs;

ii) the already small proportion of drug which penetrates the bronchial tree may be further reduced by poor inhalation technique;

iii) last but not least, chlorofluorocarbons (CFCs), such as freons contained as propellants in MDIs, are disadvantageous on environmental grounds as they have a proven damaging effect on the atmospheric ozone layer.

Dry powder inhalers (DPIs) constitute a valid alternative to MDIs for the administration of drugs to airways. The main advantages of DPIs are:

i) being breath-actuated delivery systems, they do not require co-ordination of actuation since release of the drug is dependent on the patient own inhalation;

ii) they do not contain propellants acting as environmental hazards;

iii) the quantity deposited by impaction in the oropharynx is lower. DPIs can be divided into two basic types:

i) single dose inhalers, for the administration of single subdivided doses of the active compound;

ii) multidose dry powder inhalers (MDPIs), pre-loaded with quantities of active principles sufficient for longer treatment cycles.

MDPIs are considered more convenient to the patient than single dose DPIs, not only because they provide a number of doses sufficient for longer treatment cycles but also because of their ease of use and unobtrusiveness.

Dry powder dosage forms are generally formulated by mixing the cohesive micronised drug with coarse carrier particles, giving rise to ordered mixture where the micronised active particles adhere to the surface of the carrier particles whilst in the inhaler device.

The carrier material, most commonly lactose, makes the micronised powder less cohesive and improves its flowability, making easier handling the powder during the manufacturing process (pouring, filling etc.). During inhalation, the small drug particles separate from the surface of carrier particles and penetrates into the lower lungs, while the larger carrier particles are mostly deposited in the oropharyngeal cavity.

The redispersion of drug particles from the carrier surface is regarded as the most critical factor which governs the availability of the medicament to the lungs. This will depend on the mechanical stability of the powder mix and the way this is influenced by the adhesion characteristics between the drug and the carrier and the external forces required to break up the non covalent bonds formed between adhering particles. Too strong bonds between adhering particles may prevent indeed the separation of the micronised drug particles from the surface of carrier particles. In particular, the efficiency of the redispersion process is strictly dependent on the carrier surface properties, the actual particle size of both the drug and the carrier and the drug to carrier ratio. Consequently, different approaches aimed at modulating one or more of these parameters have been proposed to promote the release of the drug particles from the carrier particles and, hence, to increase the percentage of the respirable fraction. In the prior art, the use of a ternary component, with lubricant or anti-adherent properties, has been also suggested as a solution of the technical problem.

Fisons patents GB 1242211 and GB 1381872 described powders for inhalation obtained by simple mixing of a medicament with a particle size of less than 10 microns and a coarse carrier whose particle size falls in a well defined range. They also disclosed that it may be useful to coat the surfaces of the particles and/or carrier with pharmaceutically acceptable material, such as stearic acid or polymers for giving a sustained release action to the medicament.

Chiesi WO A 87 05213 described a carrier, comprising a conglomerate of a solid water-soluble carrier and a lubricant, preferably 1% magnesium stearate, for improving the technological properties of the powder in such a way as to remedy to the reproducibility problems encountered after the repeated use of the inhaler device.

Staniforth et al. (J. Pharm. Pharmacol. 34, 141–145, 1982) observed that magnesium stearate is able to modify the adhesion of salicylic acid to sucrose but, the amount used (0.5–4.0%) destabilises the mixture to the extent that significant segregation occurs.

Kassem (London University Thesis, 1990) studied the effect of 1.5% w/w magnesium stearate or Aerosil 200 (trade name for colloidal silicon dioxide) on the de-aggregation of powders made of salbutamol sulphate and lactose. Although the 'respirable' fraction increased when magnesium stearate was added, the reported amount is too great and reduces the mechanical stability of the mixture before use. Furthermore, being magnesium stearate poorly water-soluble, its presence in such amount may rise some concerns as to a potential irritation or toxicity of this excipient, part of which can be inhaled by the patient together with the active ingredient. According to Staniforth (WO 96/23485), the reported drawbacks can be solved by adding physiologically acceptable/water-soluble additives with anti-adherent properties which do not make segregation of the active particles from the surfaces of the carrier particles during manufacturing of the dry powder and in the delivery device before use. In the said document, the anti-adherent material, preferably 1–2% leucine in particulate form, promote the release of the active particles by saturating the high energy sites of the carrier particles. Although it is generically disclosed that magnesium stearate, being highly surface active, should be added in particularly small amounts', the use of such excipient is considered not advisable.

It has now been discovered, and this is an object of the present invention, that lubricants like magnesium stearate can be advantageously and safely used as excipient for powdery pharmaceutical composition in such amount by weight based on the total weight of the powder of less than 0.5%; for steroids, the optimum amount of additive turned out to be 0.25%, whereas, for salbutamol base, it turned out to be 0.10%. Contrary to the teaching of the prior art (Peart et al. Pharm. Res. 14, S 142, 1997), 0.1% of magnesium stearate is sufficient for increasing in a significant way the fine particle dose, when salbutamol base instead of sulphate is used.

The invention also provides a method for producing a homogeneous carrier for powders for inhalation independently on the scale of mixing, the method including a step for coating the most as possible surface of the carrier particles with a little amount of lubricant. We have indeed found that it is advantageous to attain the highest as possible degree of coating of the carrier particles surface with the lubricant to increase the release of the active particles and, hence, the 'respirable' fraction. In the prior art, it was already known that the film forming properties of lubricants depend on the mixing time and significantly affect the compressibility characteristics of powders for tablets, but an advantageous relationship between the degree of coating and the 'respirable' fraction has never been reported before. We have also found, and this is another aspect of the invention, that use of lubricants in such little amount for coating the carrier, is sufficient for improving the flowability of the powder without causing mechanical stability problems of the mixture before use.

Finally we have found that the introduction of magnesium stearate in such a small amount is safe and does not produce any toxicologically relevant effect after repeated administration.

Advantageously the carrier of the invention is prepared by mixing the carrier particles and the lubricant particles for at least 2 min in a mixer in such a way as that no significant change in the particle size of the carrier particle occurs. Preferably, the carrier is mixed for at least 30 min using a rotating body mixer with a rotating speed between 5–100 r.p.m. or a stationary body mixer with a rotating mixing blade or a high-speed mixer. More preferably, the carrier is mixed for al least two hours in a Turbula mixer at 16 r.p.m.

Advantageously, the carrier particles and the lubricant particles are mixed until the degree of molecular surface coating is more than 10% as determined by water contact angle measurement. Preferably, carrier particles and lubricant particles made of magnesium stearate are mixed until the water contact angle of the 'coated' carrier particles is more than 36° corresponding to more than 10% degree of molecular surface coating; more preferably, the water contact angle should be more than 50° corresponding to more than 23% decree of molecular surface coating.

The carrier particles may be composed of any pharmacologically inert material or combinations of material acceptable for inhalation. Advantageously, the carrier particles are composed on one or more crystalline sugars. Preferably, the carrier particles are particles of α-lactose monohydrate.

Advantageously, all the carrier particles have a particle size in the range 20–1000 μm, more preferably in the range 90–150 μm.

The preferred lubricant is any type of magnesium stearate which may be crystalline or amorphous; its use is described in the embodiments of the invention by way of examples which do not limit it in any way.

Other lubricants, such as stearic acid, sodium lauryl sulphate, sodium stearyl fumarate, stearyl alcohol, sucrose monopalnitate and sodium benzoate, could turn out to be suitable depending on the type of carrier and drug used.

Advantageously, at least 50% by weight of the lubricant particles have a particle size more than 4 μm. Preferably, at least 60% of the lubricant particles made of magnesium stearate have a particle size more than 5 μm, with a specific surface area in the range 0.5–2.5 $m^2/g$ measured by Malvern.

The ratio between the carrier and the drug are mixed will depend on the type of inhaler device used and the required dose.

Advantageously, the at least 90% of the particles of the drug have a particle size less than 10 μm, preferably less than 6 μm.

Drugs include those products which are usually administered by inhalation for the treatment of respiratory diseases, i.e. β-agonists, like salbutamol, formoterol, salmeterol, terbutaline and their salts, steroids like beclometasone dipropionate, flunisolide, budesonide, others like ipratropium bromide.

In a general aspect, the invention also provides a powdery pharmaceutical composition for use in a dry powder inhaler, the powder including active particles and a carrier where the surface of the carrier particles carrying the active particles is partially coated with a film of lubricant.

EXAMPLE 1

Determination of the Suitable Amount of Magnesium Stearate to Be Added in Beclomethasone-17.21-dipropionate (BDP) Powders for Inhalation Samples of the carrier were prepared by mixing of α-lactose monohydrate (Meggle D 30) fraction 90–150 μm with 0.1%, 0.25% or 0.5% magnesium stearate for several hours in a Turbula mixer. Powders mixtures with different BDP concentrations (100, 200 and 400 μg/dose) were prepared by mixing of the carrier and the active ingredient for 30 min in a Turbula mixer at 32 r.p.m.

Multidose devices (Pulvinal®) filled with the mixtures were then tested by using a twin-stage impinger (TSI), Apparatus A (BP 93, Appendix XVII C, A194). The fine particle dose is calculated as a percentage of the total amount of drug delivered from the device (stage 1+stage 2), that reaches stage 2 of TSI. The results are summarised in Tables 1, 2 and 3 (standard deviations, S.D., given in parentheses).

No significant increase in fine particle dose is obtained from increasing the concentration of magnesium stearate above 0.25%.

TABLE 1

| Formulation (100 μg/dose) | Mg stearate (%) | Shot weight (mg) | Stage 2 (μg) | Delivered dose (μg) | Fine particle dose* (BDP %) |
|---|---|---|---|---|---|
| BDP 1 | 0.10 | 26.7 (0.3) | 22.5 (3.5) | 99.7 (0.6) | 21.9 (2.8) |
| BDP 2 | 0.25 | 26.8 (0.1) | 33.0 (5.6) | 95.3 (0.6) | 34.5 (6.2) |

TABLE 2

| Formulation (200 μg/dose) | Mg stearate (%) | Shot weight (mg) | Stage 2 (μg) | Delivered dose (μg) | Fine particle dose* (BDP %) |
|---|---|---|---|---|---|
| BDP 1 | 0 | 24.8 (0.4) | 14.2 (5.7) | 192 (14.0) | 7.3 (2.6) |
| BDP 2 | 0.10 | 26.6 (0.4) | 20.3 (4.6) | 215 (2.3) | 9.5 (2.2) |
| BDP 3 | 0.25 | 26.8 (0.6) | 48.0 (8.5) | 192 (7.8) | 25.0 (3.7) |
| BDP 4 | 0.50 | 26.7 (0.2) | 32.3 (2.3) | 193 (4.6) | 16.7 (1.0) |

TABLE 3

| Formulation (400 μg/dose) | Mg stearate (%) | Shot weight (mg) | Stage 2 (μg) | Delivered dose (μg) | Fine particle dose* (BDP %) |
|---|---|---|---|---|---|
| BDP 1 | 0 | — | — | 355 (22.8) | 7.3 (0.4) |
| BDP 2 | 0.10 | 25.4 (0.3) | 100 (11.0) | 351 (4.5) | 28.7 (3.4) |
| BDP 3 | 0.25 | 25.1 (0.4) | 142 (22.1) | 375 (9.3) | 37.9 (5.7) |
| BDP 4 | 0.50 | 25.5 (0.3) | 98 (44.7) | 421 (18.4) | 23.2 (10.3) |

EXAMPLE 2

Determination of the Suitable Amount of Magnesium Stearate to Be Added in Salbutamol Base Powders for Inhalation Samples of the carrier were prepared as reported in Example 1.

Powder mixtures containing 200 μg/dose of micronised salbutamol base were prepared by mixing of the carrier and the active ingredient for 30 min in a Turbula mixer at 32 r.p.m.

The powder mixtures were filled into inhalers and tested as reported in Example 1.

The results are summarised in Table 4.

0.1% Magnesium stearate is sufficient for increasing in a significant way (t=10.47, p<0.001) the fine particle dose, when salbutamol base instead of sulphate is used; no increase is obtained from increasing the concentration of magnesium stearate above this percentage.

TABLE 4

| Formulation (200 μg/dose) | Mg stearate (%) | Shot weight (mg) | Stage 2 (μg) | Delivered dose (μg) | Fine particle dose* (Salbutamol %) |
|---|---|---|---|---|---|
| SALB 1 | 0 | 22.4 (0.4) | 62.7 (5.3) | 185 (5.1) | 33.6 (2.9) |
| SALB 2 | 0.1 | 26.8 (0.5) | 71.3 (3.1) | 171 (5.0) | 41.8 (0.9) |
| SALB 3 | 0.25 | 26.9 (0.2) | 71.7 (6.1) | 171 (1.7) | 41.6 (3.2) |
| SALB 4 | 0.5 | 26.5 (0.5) | 68.7 (6.4) | 172 (6.0) | 39.9 (3.5) |

EXAMPLE 3

Determination of the Suitable Amount of Magnesium Stearate to Be Added in Budesonide Powders for Inhalation A sample of the carrier was prepared by mixing of α-lactose monohydrate (Meggle D 30) fraction 90–150 μm with 0.25% magnesium stearate for two hours in Turbula T100 mixer at 16 r.p.m.

Powder mixtures containing 100 μg/dose of micronised budesonide were prepared by mixing of the carrier and the active ingredient for 30 min in a Turbula mixer at 32 r.p.m.

The powder mixtures were filled into inhalers and tested as reported in Example 1.

The results are summarised in Table 5.

0.25% Magnesium stearate significantly increases the fine particle dose of budesonide (t=8.8, p<0.001);

TABLE 5

| Formulation (100 μg/dose) | Mg stearate (%) | Shot weight (mg) | Stage 2 (μg) | Delivered dose | Fine particle dose* (μg) (Budesonide %) |
|---|---|---|---|---|---|
| BUD 1 | 0 | 22.0 | — | 80.0 | 21.4 (4.7) |
| BUD 2 | 0.25 | 21.5 | — | 79.3 | 33.6 (2.6) |

*Average values obtained from three inhalers by actuating 5 shots from each inhaler.

EXAMPLE 4

Preparation of the Carrier—Study of the Mixing Conditions 40.528 kg (99.75% w/w) of α-Lactose monohydrate fraction 90–150 μm and 0.102 kg (0.25% w/w) of magnesium stearate were mixed in a Turbula mixer T 100 at 16 r.p.m. for several hours. At different mixing times samples were withdrawn and tested for uniformity of distribution of magnesium stearate, particle size, water contact angle and degree of molecular surface coating calculated according to lassie et al. (Transactions of the Faraday Society 40; 546, 1944). To validate the process, three batches (40 kg) of the carrier were prepared.

The results are reported in Tables 6 and 7, respectively.

A uniform distribution of magnesium stearate was already achieved at 60 minutes blending time (mean value, x̄, and coefficient of variation, CV%, are given); no significant change in the particle size was observed after both Malvern light-scattering and Alpine sieving analyses. By increasing the mixing time, an increase of the degree of coating occurs.

The three different batches give comparable results.

TABLE 6

| Time of min | Particle size Alpine | | Particle size Malvern | | Mg stearate uniformity | | Water contact angle | Degree coating |
|---|---|---|---|---|---|---|---|---|
| | % < 80μ | % < 90μ | % < 80μ | % < 90μ | x% | CV% | degree | % |
| 10' | — | — | — | — | — | — | 34 | 10 |
| 20' | — | — | — | — | — | — | 36 | 12 |
| 30' | 1.5 | 4.8 | 0.9 | 2.7 | 0.228 | 6.8 | 36 | 12 |
| 60' | 0.3 | 2.8 | 0.9 | 2.6 | 0.235 | 6.1 | 36 | 12 |
| 90' | 0.6 | 3.8 | 1.0 | 2.9 | 0.244 | 3.7 | 37 | 12 |
| 120' | 0.7 | 3.4 | 0.9 | 2.7 | 0.239 | 7.2 | 39 | 14 |

TABLE 6-continued

| Time of | Particle size Alpine | | Particle size Malvern | | Mg stearate uniformity | | Water contact angle | Degree coating |
|---|---|---|---|---|---|---|---|---|
| min | % < 80µ | % < 90µ | % < 80µ | % < 90µ | x% | CV% | degree | % |
| 180' | 0.8 | 4.2 | 0.8 | 2.6 | 0.246 | 2.9 | 46 | 20 |
| 240' | 1.4 | 6.3 | 0.8 | 2.6 | — | — | 48 | 21 |
| 300' | 0.7 | 6.6 | 0.9 | 2.6 | — | — | 50 | 23 |
| 360' | 0.7 | 7.0 | 1.0 | 2.8 | — | — | 51 | 24 |
| 420' | 0.9 | 7.0 | 0.9 | 2.8 | — | — | 51 | 24 |
| 480' | 0.8 | 7.5 | 0.8 | 2.6 | — | — | 51 | 24 |

α-Lactose monohydrate water contact angle 12°
Magnesium stearate water contact angle 118°

TABLE 7

| | Particle size Distribution (Alpine) | | Particle size distribution (Malvern) | | Magnesium stearate content uniformity | | Water contact |
|---|---|---|---|---|---|---|---|
| Mixing Time | % <80 µm | % <90 µm | % <80 µm | % <90 µm | x (%) | CV (%) | angle (degree) |
| CARRIER 1 | | | | | | | |
| 10 min | | | | | | | 34 |
| 20 min | | | | | | | 37 |
| 30 min | 1.5 | 4.8 | 0.9 | 2.7 | 0.228 | 6.8 | 36 |
| 60 min | 0.3 | 2.8 | 0.9 | 2.6 | 0.235 | 6.1 | 36 |
| 90 min | 0.6 | 3.8 | 1.0 | 2.9 | 0.244 | 3.7 | 37 |
| 120 min | 0.7 | 3.4 | 0.9 | 2.7 | 0.239 | 7.2 | 39 |
| CARRIER 2 | | | | | | | |
| 10 min | | | | | | | 32 |
| 20 min | | | | | | | 36 |
| 30 min | | | | | | | 38 |
| 60 min | 0.9 | 7.2 | 1.0 | 3.1 | 0.196 | 9.6 | 38 |
| 90 min | | | | | | | 40 |
| 120 min | 1.5 | 8.1 | 1.1 | 3.3 | 0.231 | 10.4 | 42 |
| CARRIER 3 | | | | | | | |
| 10 min | | | | | | | 32 |
| 20 min | | | | | | | 31 |
| 30 min | | | | | | | 33 |
| 60 min | 0.8 | 6.9 | 2.0 | 4.5 | 0.237 | 7.3 | 38 |
| 90 min | | | | | | | 42 |
| 120 min | 0.8 | 7.3 | 1.8 | 4.2 | 0.229 | 3.8 | 42 |

EXAMPLE 6

Relationship between Different Mixing Time of the Carrier and Delivered Fine Particle Dose 40.528 kg (99.75% w/w) of α-Lactose monohydrate fraction 90–150 µm and 0.102 kg (0.25% w/w) of magnesium stearate were mixed for several hours in Turbula T100 mixer at 16 r.p.m. At different mixing times, 2 kg samples were withdrawn and micronised BDP was added to each sample so that the nominal weight delivered by Pulvinal® inhaler contained 200 μg BDP. The powder mixtures were filled into inhalers and tested as reported in Example 1.

The results are reported in Table 8.

By increasing the mixing time, a significant increase at 420 min of the fine particle dose occurs ($t=5.2$, $p<0.001$).

TABLE 8

| Formulation (BDP 200 μg/dose) | BDP 1 | BDP 2 | BDP 3 |
|---|---|---|---|
| Mixing time (min) | 60 | 120 | 420 |
| Shot weight (mg) | 27.8 (0.6) | 28.1 (0.7) | 28.2 (0.5) |
| Fine particle dose* (%) | 34.1 (81) | 37.4 (4.7) | 49.5 (7.8) |
| Stage 2 (μg) | 63.1 (12.0) | 63.5 (8.1) | 102.6 (17.1) |
| Delivered dose (μg) | 188.4 (21.1) | 169.7 (7.1) | 207.2 (9.0) |

*Average values obtained from three inhalers by actuating 5 shots from each inhaler

EXAMPLE 7

Preparation of the Carrier—Comparison between Different Mixers 40.528 kg (99.75% w/w) of α-Lactose monohydrate fraction 90–150 μm and 0.102 kg (0.25% w/w) of magnesium stearate were mixed in a sigma-blade mixer for 30 min (water contact angle of 53° corresponding to 26% of molecular coating)

Powder mixtures containing 200 μg/dose of micronised BDP were prepared by mixing of the carrier and the active ingredient for 30 min in a Turbula mixer at 32 r.p.m.

The powder mixtures were filled into inhalers and tested as reported in Example 1.

The results are summarised in Table 9.

No significant difference was observed in the fine particle dose with respect to the powder obtained with the carrier prepared by using a Turbula mixer at 16 r.p.m. for 2 hours.

TABLE 9

| Formulation (200 μg/ dose) | Shot weight (mg) | Stage 2 (μg) | Delivered dose (μg) | Fine particle dose (BDP %) |
|---|---|---|---|---|
| Turbula mixer | 25.7 (2.8) | 96.2 (7.6) | 167.5 (5.7) | 57.4 (4.3) |
| Sigma-blade mixer | 26.6 (2.3) | 106.2 (11.2) | 192.1 (7.0) | 55.2 (6.0) |

EXAMPLE 8

Segregation Tendency of BDP Bulk Powder Formulation Containing 0.25% Magnesium Stearate Composition of BDP Pulvinal® (100, 200 and 400 μg/dose):

| Ingredient (mg) | Strength (μg/dose) | | |
|---|---|---|---|
| | 100 | 200 | 400 |
| BDP | 0.100 | 0.200 | 0.400 |
| α-Lactose monohydrate | 25.832 | 25.735 | 25.536 |
| Magnesium stearate | 0.067 | 0.064 | 0.064 |

The tendency of the powder to segregate was assessed according to Staniforth et al. J. (Pharm. Pharmacol. 34, 700–706, 1982).

Approximately 15 g of powder was filled into a small plastic cylinder, 80 mm long and 12 mm in diameter, closed at one end and which could be split along its axis. This allowed the characterisation of both BDP and magnesium stearate on the same level in the same bulk mixture. The tube was mounted in a vibrator (Derrinton VP4) and vibrated at 50 Hz at a force of 2 g for ten minutes. The tube was then placed in a horizontal position, divided and 15 samples, each of about 50 mg accurately weighed, taken from along its length. The samples were analysed for BDP by HPLC and for magnesium stearate by atomic absorption. The experiments were carried out in duplicate. The results are reported in Tables 10 and 11.

Typical values in coefficient of variation (CV) of BDP samples drawn from a mix judged to be satisfactory are $\leq 5.0\%$. After the imposition of an enhanced gravitational stress, BDP samples show a CV which varies from 2.7% and 7.8%. Despite the intense vibration, these variations have not increased significantly and are consistent with good inhaler performance when judged in terms of dose uniformity. Samples taken from the top of the bed are very similar to the bottom samples.

In the case of magnesium stearate, variability between samples was somewhat greater than for BDP due to its lower concentration. However, no consistent change in the uniformity of distribution occurred after vibration and, as with BDP, the content of samples drawn from the top of the bed were not different to those drawn from the bottom. It can be concluded that the ordered mix is very stable and no segregation of BDP and magnesium stearate occurs.

TABLE 10

| | DRUG ASSAY (μg /mg) | | | | | |
|---|---|---|---|---|---|---|
| | BDP 400 μg/dose | | BDP 200 μg/dose | | BDP 100 μg/dose | |
| SAMPLE | 1 | 2 | 1 | 2 | 1 | 2 |
| Top of Cylinder | | | | | | |
| 1 | 17.9 | 17.3 | 8.6 | 8.5 | 4.4 | 4.4 |
| 2 | 20.5 | 17.1 | 7.5 | 7.6 | 3.5 | 3.5 |
| 3 | 16.9 | 17.6 | 7.7 | 7.7 | 3.7 | 3.9 |
| 4 | 18.0 | 16.9 | 7.7 | 7.8 | 3.8 | 3.9 |
| 5 | 17.0 | 17.0 | 7.5 | 9.0 | 4.1 | 4.2 |
| 6 | 17.2 | 17.1 | 7.6 | 7.8 | 3.9 | 3.8 |
| 7 | 17.4 | 17.6 | 7.4 | 8.1 | 3.7 | 3.8 |
| 8 | 17.2 | 17.1 | 7.6 | 7.7 | 4.2 | 3.8 |
| 9 | 16.8 | 17.3 | 7.7 | 7.6 | 4.5 | 3.9 |
| 10 | 16.9 | 16.5 | 8.3 | 8.0 | 3.6 | 3.8 |
| 11 | 16.9 | 18.9 | 7.8 | 8.0 | 4.4 | 4.0 |
| 12 | 21.1 | 18.1 | 7.9 | 7.9 | 3.9 | 3.9 |
| 13 | 17.3 | 17.5 | 7.8 | 7.3 | 3.9 | 4.2 |
| 14 | 19.4 | 17.1 | 7.7 | 7.7 | 4.2 | 4.1 |
| 15 | 18.0 | 19.1 | 7.8 | 8.0 | 4.4 | 3.9 |
| Bottom of Cylinder | | | | | | |
| Mean | 17.9 | 17.5 | 7.8 | 7.9 | 4.0 | 3.9 |
| SD | 1.4 | 0.8 | 0.2 | 0.4 | 0.3 | 0.2 |
| CV (%) | 7.6 | 4.3 | 2.7 | 5.0 | 7.8 | 4.7 |

TABLE 11

| | MAGNESIUM ASSAY (μg/mg) | | | | | | | | |
|---|---|---|---|---|---|---|---|---|---|
| | BDP 400 μg/dose | | | BDP 200 μg/dose | | | BDP 100 μg/dose | | |
| SAMPLE | 1 | 2 | UN-VIBRATED | 1 | 2 | UN-VIBRATED | 1 | 2 | UN-VIBRATED |
| Top of cylinder | | | | | | | | | |
| 1 | 0.115 | 0.124 | 0.101 | 0.101 | 0.092 | 0.125 | 0.082 | 0.076 | 0.103 |
| 2 | 0.116 | 0.122 | 0.103 | 0.105 | 0.091 | 0.121 | 0.105 | 0.073 | 0.150 |
| 3 | 0.114 | 0.123 | 0.107 | 0.108 | 0.093 | 0.125 | 0.096 | 0.091 | 0.104 |
| 4 | 0.113 | 0.119 | 0.109 | 0.100 | 0.093 | 0.118 | 0.107 | 0.085 | 0.101 |
| 5 | 0.114 | 0.126 | 0.110 | 0.115 | 0.089 | 0.135 | 0.094 | 0.083 | 0.110 |
| 6 | 0.108 | 0.108 | 0.107 | 0.103 | 0.100 | 0.208 | 0.098 | 0.080 | 0.109 |
| 7 | 0.111 | 0.113 | 0.110 | 0.111 | 0.096 | 0.107 | 0.104 | 0.114 | 0.109 |
| 8 | 0.118 | 0.108 | 0.108 | 0.107 | 0.096 | 0.101 | 0.102 | 0.076 | 0.102 |
| 9 | 0.107 | 0.104 | 0.106 | 0.106 | 0.094 | 0.102 | 0.099 | 0.082 | 0.103 |
| 10 | 0.113 | 0.119 | 0.107 | 0.094 | 0.097 | 0.101 | 0.104 | 0.081 | 0.109 |
| 11 | 0.114 | 0.120 | 0.109 | 0.091 | 0.094 | 0.096 | 0.090 | 0.086 | 0.105 |
| 12 | 0.116 | 0.117 | 0.105 | 0.083 | 0.093 | 0.098 | 0.100 | 0.084 | 0.107 |
| 13 | 0.112 | 0.101 | 0.103 | 0.114 | 0.077 | 0.100 | 0.092 | 0.079 | 0.104 |
| 14 | 0.115 | 0.104 | 0.107 | 0.081 | 0.095 | 0.097 | 0.091 | 0.072 | 0.107 |
| 15 | 0.106 | 0.097 | 0.102 | 0.080 | 0.076 | 0.100 | 0.086 | 0.085 | 0.105 |

TABLE 11-continued

| | MAGNESIUM ASSAY (µg/mg) | | | | | | | | |
|---|---|---|---|---|---|---|---|---|---|
| | BDP 400 µg/dose | | | BDP 200 µg/dose | | | BDP 100 µg/dose | | |
| SAMPLE | 1 | 2 | UN-VIBRATED | 1 | 2 | UN-VIBRATED | 1 | 2 | UN-VIBRATED |
| Bottom of Cylinder | | | | | | | | | |
| Mean | 0.113 | 0.114 | 0.106 | 0.100 | 0.092 | 0.116 | 0.097 | 0.083 | 0.109 |
| SD | 0.003 | 0.009 | 0.003 | 0.012 | 0.007 | 0.028 | 0.007 | 0.010 | 0.012 |
| (CV %) | 3.1 | 8.2 | 2.7 | 11.6 | 7.3 | 24.6 | 7.6 | 12.0 | 10.9 |

EXAMPLE 9

Fine Particle Delivery of Magnesium Stearate

A batch of BDP 400 µg/shot powder was prepared by mixing of the drug and the carrier (lactose/magnesium stearate 99.75/0.2.5% w/w) under the conditions reported in Example 1. Devices were filled with the mixture and the fine particle delivery of magnesium stearate was determined using a TSI apparatus. The results are reported in Table 12.

TABLE 12

| | Shot weight (mg) | Total Mg stearate (%) | Total Mg stearate (µg) | Mg stearate stage 2 (µg) |
|---|---|---|---|---|
| Mean | 26.4 | 0.259 | 68 | 19 |
| S.D. | 0.31 | 0.017 | 4.18 | 2.39 |
| CV % | 1.18 | 6.52 | 6.13 | 12.5 |

Considering the low concentration of magnesium stearate in the formulation and the quantity found in stage 2 of TSI, the amount to be respirable will be very low.

This amount has been demonstrated to be safe after toxicity studies in dog.

Furthermore, acute and long term tolerance trials were carried out to evaluate toxicity of magnesium stearate in humans.

In the former, 18 healthy volunteers, included in a double blind randomised controlled cross-over design study, received a single dose containing 25.72 mg of lactose and 0.065 mg of magnesium stearate via Pulvinal® inhaler. The introduction of 0.25% magnesium stearate in powdery pharmaceutical formulation resulted to be safe.

In the long term randomised, controlled, parallel group study, the safety of magnesium stearate as a carrier was compared to that of lactose. 28 Mild asthmatic patients were treated for 3 months with 400 µg BDP b.i.d. delivered either with Pulvinal®, containing 0.065 mg of magnesium stearate per dose, or another commercially available DPI, containing 25.536 mg of lactose per dose. Bronchial biopsies and broncho-alveolar lavages performed at the beginning and at the end of trial did not evidence accumulation of magnesium in bronchi or in alveolar cells either in Pulvinal® or control group.

What is claimed is:

1. A powder for use in a dry powder inhaler, the powder consisting of an active ingredient and a carrier, the carrier consisting of one or more crystalline sugars in the form of particles of size within the range 20 and 1000 µm mixed with a lubricant selected from the group consisting of magnesium stearate, stearic acid, sodium stearyl fumarate, stearyl alcohol, and sucrose monopalmitate, wherein the lubricant coats the carrier particles to an extent such that the coated particles have a water contact angle of at least 36° and is present in an amount within the range of 0.1–0.5 percent by weight of the composition.

2. A powder according to claim 1 in which the lubricant coats the carrier particles to an extent such that the coated particles have a water contact angle of at least 39°.

3. A powder according to claim 2 in which the lubricant coats the carrier particles to an extent such that the coated particles have a water contact angle more than 50°.

4. A powder according to claim 1 wherein the lubricant is magnesium stearate in an amount of 0.10 and 0.25 percent by weight.

5. A powder according to claim 4 wherein magnesium stearate is a crystalline or an amorphous material.

6. A powder according to claim 4 wherein magnesium stearate is of animal or vegetable origin.

7. A powder according to claim 1 wherein the crystalline sugar is made of α-lactose monohydrate.

8. A powder according to claim 1 wherein the carrier particles have a size within the range 90 and 150 µm.

9. A powder according to claim 1 wherein the active ingredient has a particle size less than 10 µm.

10. A powder according to claim 1 wherein the active ingredient includes a steroid.

11. A powder according to claim 10 wherein the active ingredient is selected from the group consisting of beclometasone dipropionate, budesonide and its epimers and flunisolide.

12. A powder according to claim 1 wherein the active ingredient includes a β2-agonist selected from the group consisting of salbutamol base, formoterol, salmeterol, terbutaline and the salts thereof.

13. A carrier for use in making a powder for use in a dry powder inhaler, said carrier consisting of one or more crystalline sugars and being in the form of particles of a size within the range 20 and 1000 µm mixed in a mixer apparatus with a lubricant selected from the group consisting of magnesium stearate, stearic acid, sodium stearyl fumarate, stearyl alcohol, and sucrose monopalmitate, wherein the lubricant coats the carrier particles to an extent such that the coated particles have a water contact angle of at least 36° and is present in an amount within the range of 0.1–0.5 percent by weight of the composition.

14. A carrier according to claim 13 wherein the lubricant coats the carrier particles to an extent such that the coated particles have a water contact angle of at least 39°.

15. A method for producing a carrier for use in making a powder for use in a dry powder inhaler, such carrier consisting of one or more crystalline sugars and being in the form of particles of a size within the range 20 and 1000 µm mixed with a lubricant selected from the group consisting of magnesium stearate, stearic acid, sodium stearyl fumarate, stearyl alcohol, and sucrose monopalmitate, wherein the lubricant coats the carrier particles to an extent such that the coated particles have a water contact angle of at least 36° and is present in an amount within the range of 0.1–0.5 percent by weight of the composition, the method including the step of mixing in a mixer apparatus carrier particles of a size within the range 20 and 1000 μm with 0.1–0.5 percent by weight of a lubricant to provide a coating on the carrier particles to an extent such that the coated particles have a water contact angle of at least 36°.

16. A method according to claim 15 wherein the carrier particles and the lubricant are mixed using a tumbling mixer selected from the group consisting of a rotating body mixer and a stationary body mixer with a rotating mixing blade for at least 120 min.

17. A method according to claim 16 wherein the tumbling mixer is operated at a mixing speed within the range of 16 to 32 r.p.m.

18. A method according to claim 15 wherein the carrier particles and the lubricant are mixed in a high-speed mixer.

19. A powder according to claim 13 in which the lubricant coats the carrier particles to an extent such that the coated particles have a water contact angle of more than 50°.

* * * * *